United States Patent
Korodi

(10) Patent No.: US 9,248,046 B2
(45) Date of Patent: *Feb. 2, 2016

(54) EYE DROP DEVICE

(71) Applicant: Miklos B. Korodi, Dublin, OH (US)

(72) Inventor: Miklos B. Korodi, Dublin, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/629,068

(22) Filed: Feb. 23, 2015

(65) Prior Publication Data

US 2015/0164688 A1  Jun. 18, 2015

Related U.S. Application Data

(63) Continuation of application No. 14/455,432, filed on Aug. 8, 2014, now Pat. No. 8,961,480, which is a continuation of application No. PCT/US2013/054549, filed on Aug. 12, 2013.

(60) Provisional application No. 61/681,979, filed on Aug. 10, 2012.

(51) Int. Cl.
*A61F 9/00* (2006.01)
*A61B 19/00* (2006.01)

(52) U.S. Cl.
CPC ........... *A61F 9/0026* (2013.01); *A61B 19/5202* (2013.01); *A61B 2019/521* (2013.01); *A61F 2220/0025* (2013.01)

(58) Field of Classification Search
CPC .............................. A61F 9/0008; A61F 9/0026
USPC .................................................... 604/302, 295
See application file for complete search history.

(56) References Cited

U.S. PATENT DOCUMENTS

| 5,558,653 | A | 9/1996 | Lindstrom |
|---|---|---|---|
| 6,659,943 | B2 | 12/2003 | Watanabe et al. |
| 7,191,916 | B2 | 3/2007 | Clifford et al. |
| 8,231,995 | B2 | 7/2012 | Park et al. |
| 2002/0016576 | A1 | 2/2002 | Lee |
| 2007/0052926 | A1 | 3/2007 | Li |
| 2010/0286634 | A1 | 11/2010 | Marx |
| 2011/0257631 | A1 | 10/2011 | Murphy |
| 2012/0062830 | A1 | 3/2012 | Waters |

*Primary Examiner* — Leslie Deak
*Assistant Examiner* — Kai Weng
(74) *Attorney, Agent, or Firm* — Standley Law Group LLP

(57) ABSTRACT

An eye drop device and a method of applying eye drops to the eye are disclosed herein. An exemplary embodiment of the device contains a main housing having an interior and exterior with a top opening sized to surround the eye and a bottom opening sized to accept the tip of an eye drop vial. The device also preferably contains a cavity for accepting the battery and an LED positioned within the interior of the main housing. A switch may be used to energize the LED. The method includes the steps of attaching an eye drop vial to the main housing, positioning the device over the eye, energizing the LED, and applying the eye drops.

8 Claims, 4 Drawing Sheets

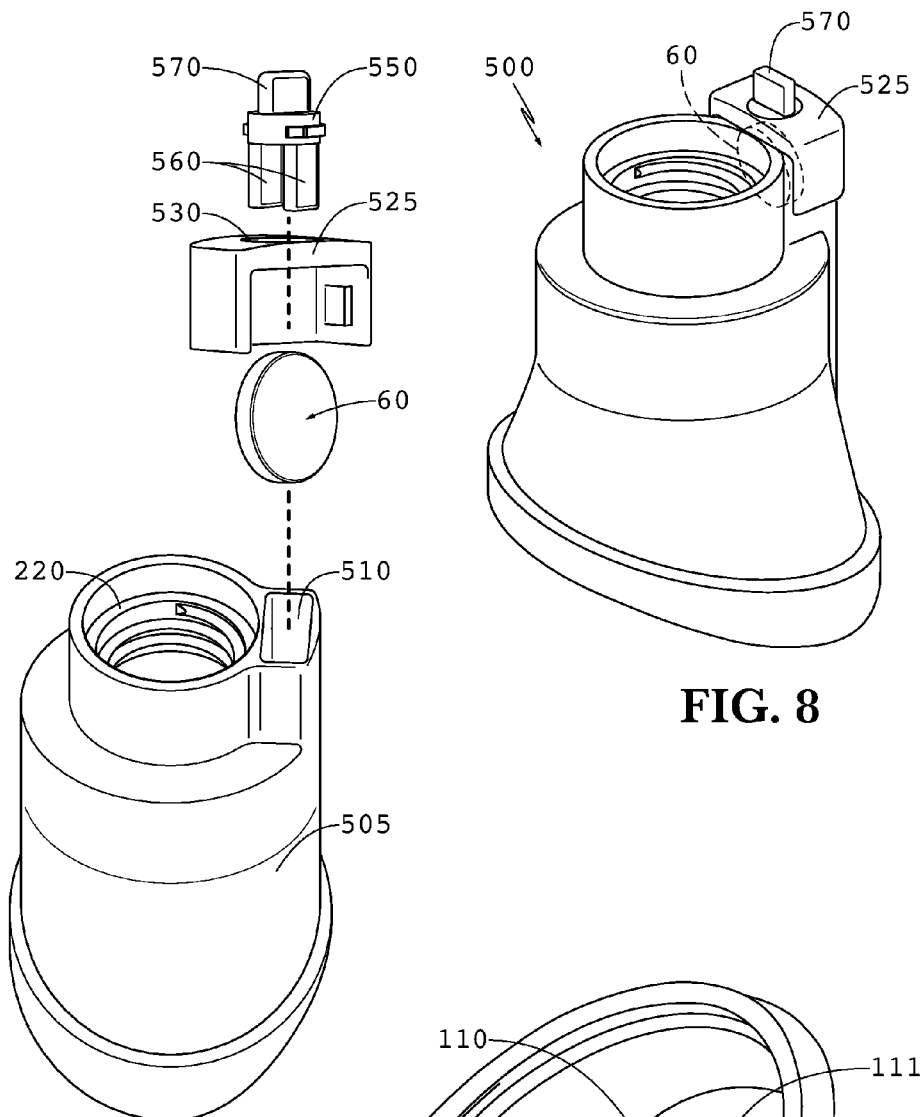

EYE DROP DEVICE

CROSS-REFERENCE TO RELATED APPLICATIONS

This application is a continuation of U.S. non-provisional application Ser. No. 14/455,432, filed 8 Aug. 2014, now U.S. Pat. No. 8,961,480, which is in turn a by-pass continuation of PCT/US2013/054549, filed on 12 Aug. 2013, that claims priority to U.S. provisional application 61/681,979, filed on 10 Aug. 2012. Each of the foregoing applications is incorporated herein by reference.

TECHNICAL FIELD

Embodiments generally relate to an eye drop device for assisting users in the application of drops to the eyeball, particularly by presenting an energized LED device in the user's field of vision near the location of the drop being dispensed.

BACKGROUND OF THE ART

Eye drops are common substances used to treat a variety of ailments or to numb the eye for testing or medical procedures. Generally, the user would tilt their head backwards (to look towards the sky or ceiling), hold a portion of their eye or eyelid open, and insert the drops into the eyeball. For some users however, it can be difficult to administer drops directly onto the eye. This could be because of sensitive eyes or eyes that cannot open very wide to allow the drops to be inserted. Some users may suffer a medical condition such as glaucoma or cataracts and thus have trouble keeping their eyes open during the process, especially without any assistance. Other users may have an injury to the eyes that prevents them from opening them for washing, cleaning, or treatment.

SUMMARY OF THE EXEMPLARY EMBODIMENTS

Exemplary embodiments provide an eye drop device which helps the user to keep their eye open while inserting eye drops. The device preferably contains a bottom opening for accepting the eye drop vial and a top opening for surrounding the eyeball. Between the bottom opening and top opening may be a cavity containing an LED (or other illumination source). The LED may be energized once the device is positioned against the eyeball so that the user's eye is drawn to the light and remains open while the drops are inserted into the eye. The LED may be energized manually through the use of a manual switch. Alternatively, the LED may be in electrical communication with a gravity-actuated switch such that once the device is inverted and placed on the eyeball, the LED is energized automatically.

The foregoing and other features and advantages of the present invention will be apparent from the following more detailed description of the particular embodiments, as illustrated in the accompanying drawings.

BRIEF DESCRIPTION OF THE DRAWINGS

A better understanding of an exemplary embodiment will be obtained from a reading of the following detailed description and the accompanying drawings wherein identical reference characters refer to identical parts and in which:

FIG. 7 is an exploded view of another embodiment of the eye drop device;

FIG. 8 is a bottom perspective view of the embodiment shown in FIG. 7 where a portion of the device is shown transparent to illustrate the internal components;

FIG. 9 is a top perspective view of the embodiment shown in FIGS. 7 and 8 where a portion of the device is shown transparent to illustrate the internal components.

DETAILED DESCRIPTION

Figure 1:
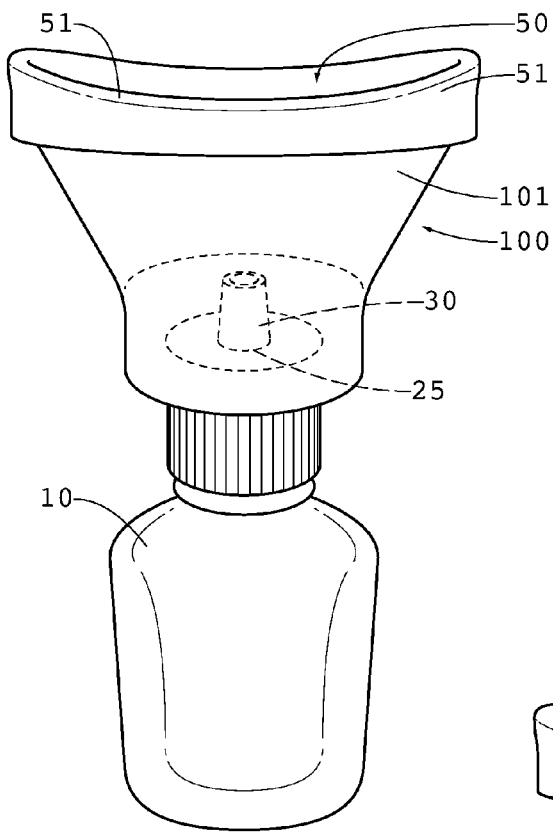
FIG. 1 is a front planar view of one embodiment of the eye drop device attached to a traditional eye drop vial.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a front planar view of one embodiment of the eye drop device 100 attached to a traditional eye drop vial 10. In this embodiment, the main housing 101 of the eye drop device 100 contains a bottom opening 25 for accepting the applicator tip 30 of the eye drop vial 10. A top opening 50 is positioned opposite the bottom opening 25 and is sized to surround the eyeball. The top opening 50 preferably contains a rounded and preferably smooth perimeter 51 so that it is comfortable to place atop the eyeball.

Figure 2:
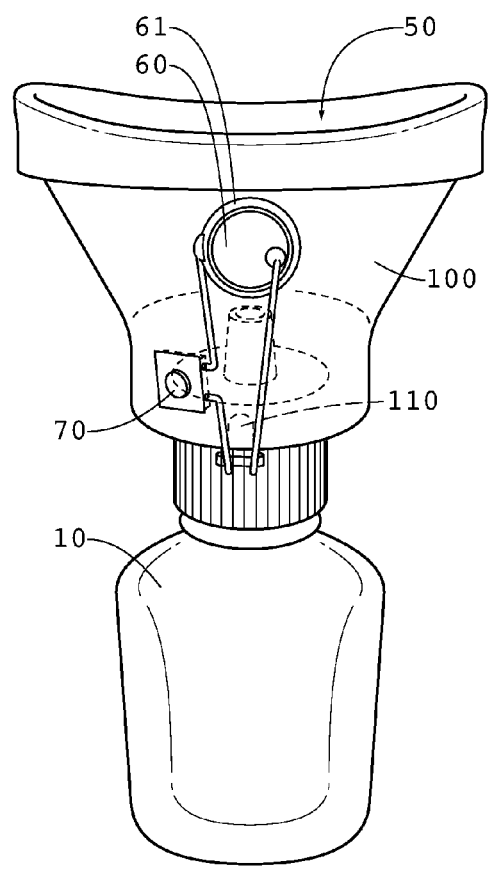
FIG. 2 is a rear planar view of the embodiment shown in FIG. 1.

FIG. 2 is a rear planar view of the embodiment shown in FIG. 1. The battery 60 may be attached to the eye drop device 100 and may be positioned within a cavity 61. A switch 70 and the LED 110 (or other illumination source) may be in electrical communication with the battery 60, such that activation of the switch 70 causes the LED 110 to illuminate.

Figure 3:
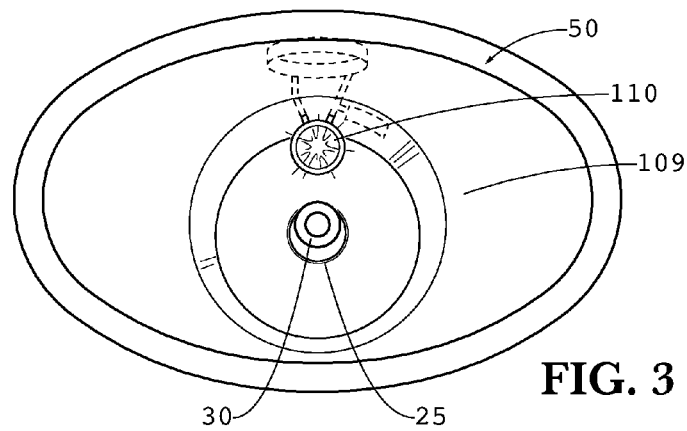
FIG. 3 is a top planar view of the embodiment shown in FIG. 1.

FIG. 3 is a top planar view of the embodiment shown in FIG. 1. A cavity 109 is located between the bottom opening 25 and the top opening 50. The LED 110 is preferably positioned within the cavity 109 and preferably near the bottom opening 25.

Figure 4A:
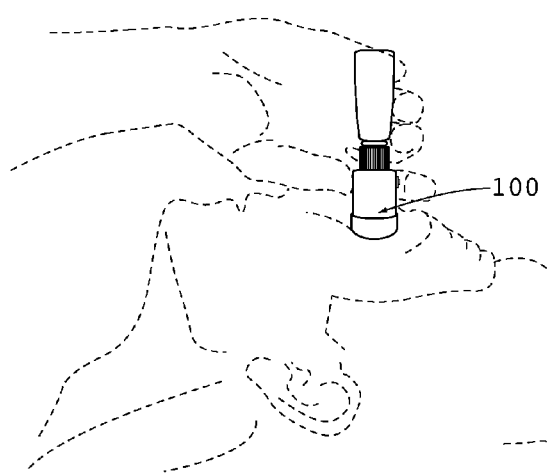
FIG. 4A is a side illustration of the embodiment shown in FIG. 1 prior to illuminating the LED and inserting the drops.

FIG. 4A is a side illustration of the embodiment shown in FIG. 1 prior to illuminating the LED 110 and inserting the drops. Generally speaking, after the eye drop vial 10 has been inserted into the device 100, a user may tilt their head back and place the perimeter 51 of the top opening 50 around the eyeball. In an exemplary embodiment, the user can place a portion of the perimeter 51 of the top opening 50 against the top, bottom, or top and bottom eyelid(s) and apply pressure so as to hold the eye open during application of the drops.

Figure 4B:
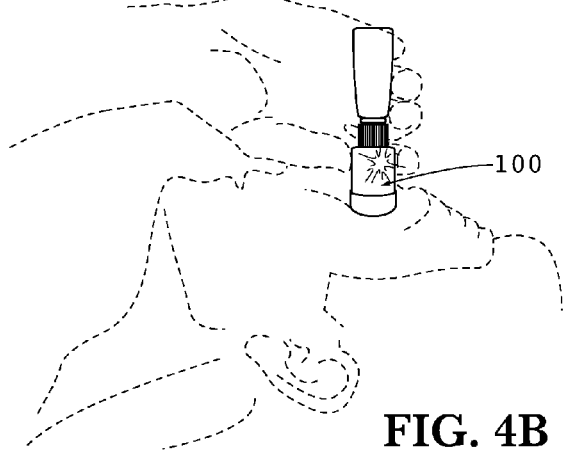
FIG. 4B is a side illustration of the embodiment shown in FIG. 1 while illuminating the LED and inserting the drops.

FIG. 4B is a side illustration of the embodiment shown in FIG. 1 while illuminating the LED 110 and inserting the drops. It has been discovered, that illumination of the LED 110 within the cavity 109 of the device 100 causes the eye to open and stay focused on the light of the LED 110. This phenomena allows users who may have sensitive eyes or eyes that have difficulty staying open to insert eye drops into their eyes in a more quick and easy manner. In this particular embodiment, the user may energize the LED 110 themselves by actuating the switch 70 while squeezing the eye drop vial 10. Alternatively, a second person could hold the device 100 in place while actuating the switch 70 and squeezing the eye drop vial 10. As discussed below, the switch used with any particular embodiment may not require a manual actuation to energize the LED 110.

Figure 5:
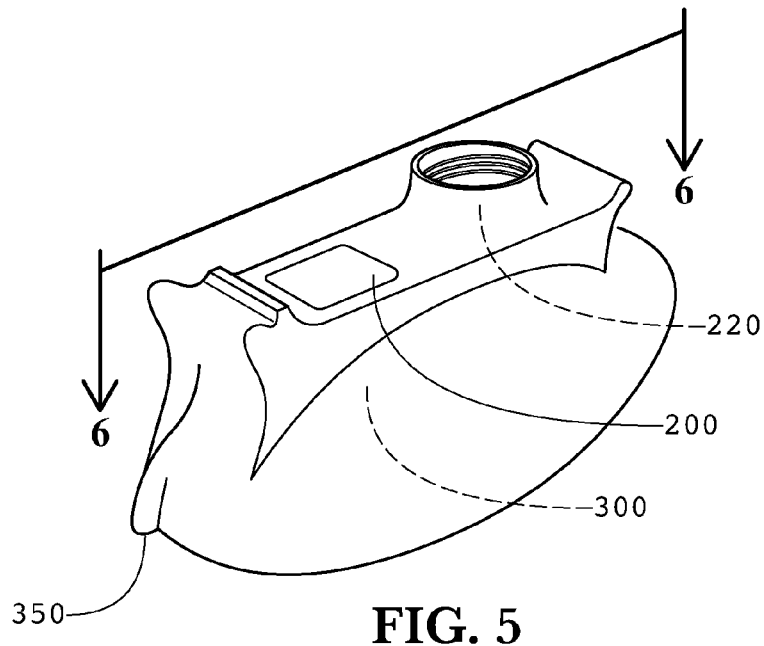
FIG. 5 is a perspective view of another embodiment of the eye drop device and indicating the section line 6-6.

FIG. 5 is a perspective view of another embodiment of the eye drop device 300. In this embodiment, the device 300 contains an access panel 200 for obtaining access to and/or installing the electrical components, such as providing access to a cavity for the battery 60 (not shown in this view). A threaded collar 220 is sized and adapted to accept the threaded neck of an eye drop vial 10. A positioning tab 350 is preferably placed on the device 300 for assisting the user in positioning the device when in use. This figure also indicates the location of the section line 6-6

Figure 6:
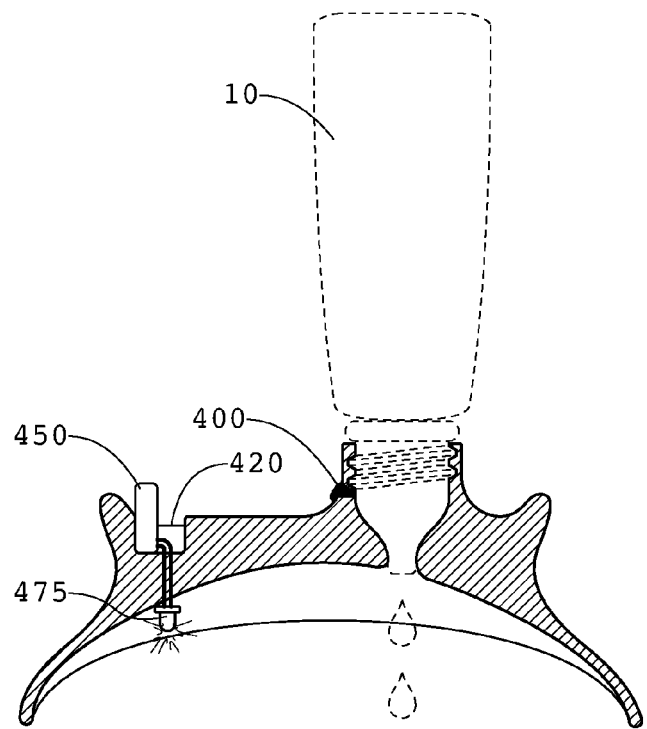
FIG. 6 is a sectional view of the embodiment shown in FIG. 5 with a traditional eye drop vial inserted, taken along the section line 6-6.

FIG. 6 is a sectional view of the embodiment shown in FIG. 5 with a traditional eye drop vial 10 inserted and taken along the section line 6-6. Here, a pressure sensitive switch 400 may be used such that the switch is activated when the eye drop vial 10 is inserted. This switch 400 is preferably in electrical communication with a battery 450, a gravity activated switch 420, and the LED 475 such that once the switch 400 is energized and the device 300 is inverted (i.e. oriented with the eye drop vial 10 on top) the LED 475 will automatically illuminate. Some embodiments may utilize a pressure contact switch rather than the gravity activated switch 420 such that the LED is illuminated when the device is pressed against the ocular cavity of the user.

FIG. 7 is an exploded view of another embodiment of the eye drop device 500. Here, a main housing 505 contains a threaded collar 220 and a cavity 510 positioned adjacent to the threaded collar 220. The cavity 510 is sized to accept the battery 60 and at least a portion of a pair of prongs 560 which extend from the switch 550. The prongs 560 are preferably spaced so as to surround the battery 60, such that when the switch tab 570 is rotated, the battery 60 rotates as well. A cap 525 preferably contains an aperture 530 for accepting the prongs 560 and is sized to cover the cavity 510 and secure the switch 550 and battery 60 within the cavity 510.

FIG. 8 is a bottom perspective view of the embodiment shown in FIG. 7 where the main housing 505 of the device 500 is shown transparent to illustrate the internal components. Preferably, once the battery 60 is inserted into the cavity 510, the cap 525 covers the battery 60 and accepts the switch 550. The switch tab 570 should preferably extend below the cap 525 so that it can be accessed by a user.

FIG. 9 is a top perspective view of the embodiment shown in FIGS. 7 and 8 where the main housing 505 of the device 500 is shown transparent to illustrate the internal components. The LED 110 is placed within the cavity of the main housing 505 and contains a first 111 and a second 112 lead. In this embodiment, the first 111 and second 112 lead are each routed to separate terminals on the battery 60. As discussed above, the battery 60 is preferably sandwiched in between the prongs 560 of the switch such that as the switch tab 570 is rotated, the battery 60 rotates as well. In this embodiment, when the battery 60 is in a first rotational position (i.e. the powered position), the battery 60 terminals are in contact with the first 111 and second 112 LED leads and the LED 110 is energized. However, once the switch 550 is rotated (which rotates the battery 60 away from the first 111 and second 112 LED leads) the battery 60 is no longer in contact with the first 111 and second 112 LED leads such that the LED 110 is no longer energized (i.e. unpowered position(s)).

The main housing of the device can be any rigid or semi-rigid material, preferably a plastic of some type. It may be preferable for the device to be dark colored or tinted, so that the interior cavity of the device (containing the LED) is darker than the surrounding environment so that the LED is more impactful and/or visible to the user. In some embodiments the main housing may be opaque, while in some others it may be at least semi-transparent. Any color LED may be used with the various embodiments shown.

As used herein, the term 'eye drop vial' is not limited to those eye drop products that are commercially available to consumers, but would also include any dropper device, such as those commonly found in chemistry labs or any eye doctor/surgeon's office. All that is required is to insert the tip of the dropper into the bottom opening 25, either before or after the device has been positioned over a user's eye. If inserted prior to positioning the device it can easily be held in place; a simple friction fit or interference fit will hold the dropper in place within the bottom opening 25 if there are no threads present on the eye drop vial.

It should also be noted that the term 'eye drop vial' does not imply any specific type of bottle or vial nor any specific type of solution within the bottle or vial. It can be everything from distilled water to numbing agents or active medicines.

Having shown and described a preferred embodiment of the invention, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention. It is the intention, therefore, to limit the invention only as indicated by the scope of the claims.

What is claimed is:

1. A device for dispensing drops into an eye of a user from a vial having a dispensing tip, the device comprising:
   a main housing, having a first opening that is sized and adapted to surround the user's eye and a second opening that is sized and adapted to receive the dispensing tip, directing the dispensing tip toward the first opening, the main housing further comprising a continuous wall that effectively encloses an interior of the main housing that faces the first opening;
   a switch, arranged in the main housing; and
   an LED, arranged on the interior of the main housing and directed toward the first opening, the LED in electrical communication with the switch such that activation of the switch causes the LED to illuminate.

2. The dispensing device of claim 1, wherein:
   the first opening contains a rounded perimeter edge.

3. The dispensing device of claim 1, wherein:
   the second opening contains a threaded collar adapted to receive the dispensing tip of the vial.

4. The dispensing device of claim 1, wherein:
   the switch is a pressure switch arranged relative to the second opening such that reception of the dispensing tip activates the switch and removal of the dispensing tip deactivates the switch.

5. The dispensing device of claim 4, further comprising:
   a gravity switch arranged in electrical communication with the pressure switch and the LED such that the LED is illuminated only when the dispensing tip is in the second opening and the vial is inverted.

6. The dispensing device of claim 1, wherein:
   the switch is a gravity switch arranged such that the LED is illuminated when the main housing is in a position where the second opening is located above the first opening.

7. The dispensing device of claim 1, wherein:
   the LED is positioned near the second opening.

8. The dispensing device of claim 1, wherein:
   the continuous wall of the main housing is formed of an opaque material.

* * * * *